(12) United States Patent
Ferguson

(10) Patent No.: US 6,264,619 B1
(45) Date of Patent: Jul. 24, 2001

(54) KIT FOR DRAWING A BLOOD SAMPLE

(75) Inventor: Margie Ferguson, East Orange, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/387,816

(22) Filed: Sep. 1, 1999

(51) Int. Cl.[7] .................................................. A61B 5/00
(52) U.S. Cl. .......................................... 600/573; 206/569
(58) Field of Search .................................... 600/573, 578, 600/583, 584; 206/569; 606/181

(56) References Cited

U.S. PATENT DOCUMENTS

| | | | |
|---|---|---|---|
| 3,013,656 | * 12/1961 | Murphy, Jr. | 206/569 |
| 3,203,540 | * 8/1965 | Kaut et al. | 206/569 |
| 4,192,919 | 3/1980 | Raghavachari . | |
| 4,886,071 | * 12/1989 | Mehl et al. | 600/573 |
| 5,020,665 | * 6/1991 | Bruno | 206/366 |
| 5,086,783 | * 2/1992 | Macors et al. | 600/578 |
| 5,117,981 | * 6/1992 | Crawford et al. | 206/570 |
| 5,178,157 | * 1/1993 | Fanlo | 600/576 |
| 5,520,041 | * 5/1996 | Haswell | 73/29.04 |
| 5,704,917 | * 1/1998 | Utterberg | 604/180 |
| 6,071,294 | * 6/2000 | Simons et al. | 606/181 |

* cited by examiner

Primary Examiner—John P. Lacyk
Assistant Examiner—Pamela L. Wingood
(74) Attorney, Agent, or Firm—Richard E. Brown

(57) ABSTRACT

A kit containing all the materials needed to take a blood sample from a neonatal patient, a pediatric patient, a juvenile patient or an adult patient. The materials are supplied in a plastic package suitable for sterilization.

10 Claims, 1 Drawing Sheet

KIT FOR DRAWING A BLOOD SAMPLE

BACKGROUND OF THE INVENTION

1. Field of Invention

This invention relates to blood samples and more particularly relates to a combination of materials used in drawing a blood sample.

2. Background of the Invention

Many medical procedures call for analysis of a patient's blood and various reports have appeared disclosing devices and procedures for drawing blood samples and preparing them for storage, transportation or analysis. The one common feature of all reports on blood sampling is the attention paid to protecting against any contact between the patient's blood and the phlebotomist.

The equipment needed for blood sampling varies according to the analytical procedure for which the sample is intended. For example, some tests require only a single drop of blood while others require milliliter quantities divided into several portions. Some require anticoagulants, others require procoagulants. All require aseptic conditions during sampling and accordingly, employ various items to protect against infection and contact between the patient's blood and the phlebotomist. Thus, in modern medical practice, the skin puncture site must be sterilized prior to puncture and the puncture site aseptically covered after sampling. To avoid contact with the sample, disposable gloves are routinely worn by the phlebotomist.

Blood sampling has traditionally been performed by initially locating the necessary equipment, generally supplied in various packages by different suppliers, then arranging the individual items in a convenient and easily reached order prior to sampling. This operation has the obvious disadvantage of inefficiency compounded by the danger of beginning the blood draw without an essential component at hand. There is a definite need in the art of blood sampling for overcoming the above disadvantages of piecemeal gathering of the essential tools. It is toward fulfillment of this need that the present invention is directed.

SUMMARY OF THE INVENTION

A kit of materials for drawing a blood sample includes means for sterilizing a patient's skin, means for penetrating the patient's skin, holding means for containing the sample taken and packaging means for all of the components.

The kit may also contain any other component needed for the intended purpose of the kit. Thus, other components may be a fabric, such as gauze, for removing the sterilant after the sterilizing step or for covering the puncture wound after the sample is drawn. Other optional components of the kit are disposable gloves, a support for the holding means after the sample is taken, securing means to maintain the fabric in place over the puncture wound, and a tourniquet to promote blood flow.

A preferred skin penetrating means is a needle or a lancet and a preferred holding means is a tube or vial. The preferred sterilizing means is a gauze containing a disinfectant, such as alcohol or antibacterial, and the preferred securing means is an adhesive tape.

Thus, the invention provides an array of conventional blood sampling components combined in a single convenient package which obviates the necessity and inefficiency of prior locating and arranging of all components that will be needed.

BRIEF DESCRIPTION OF THE DRAWING

The FIGURE illustrates a typical package of blood sampling components arranged in kit form.

DETAILED DESCRIPTION

Figure 1:
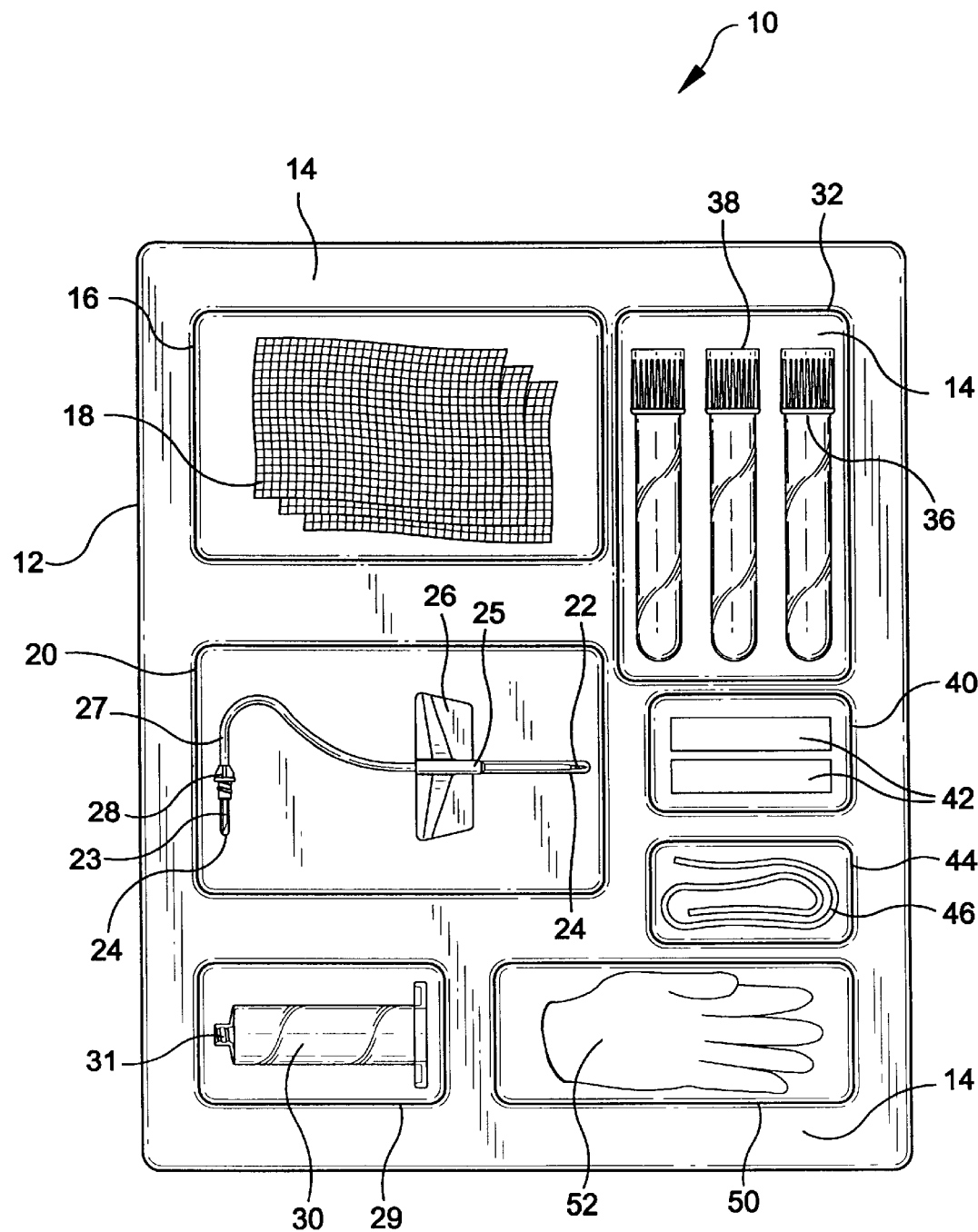

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The kit of the invention contemplates a package of components for drawing a blood sample. Without intending any limitation thereof, preferred kits are directed toward blood sampling from an adult patient, a juvenile patient, a neonatal patient and a diabetic patient.

A first component of the kit of the invention for taking a blood sample is a means for sterilizing the patient's skin in the area of intended puncture. A typical and conventional sterilizing means is a piece of fabric commonly referred to as a gauze. The gauze preferably has a sterilant occluded therein and optionally may be attached to a grasping portion. A preferred sterilant is alcohol, although other sterilpnts such as antibacterial agents may be used. Exemplary of suitable antibacterials are the bisbiguanides, of which chlorhexidine is the best known member. The chlorhexidine may preferably be provided as a soluble salt in aqueous or alcoholic solution.

The skin penetrating means for initiation of blood flow may be a conventional lancet or may be any of a variety of conventional devices which includes a needle. The needle may be single or double ended and may be of any gauge, preferably 21 or 23 gauge. It preferably has a safety sleeve thereover, may be attached to a needle hub, and preferably is used with a conventional tube holder. The needle may also be part of a conventional syringe assembly including barrel and plunger. Also, as known in the art, the penetrating means may be part of a conventional blood collection set in which a penetrating needle having a grasping means, such as wings, is connected via a hub and tubing to a delivery needle for puncture of a septum of an evacuated tube.

The holding means of the kit may be any type of container for receiving the sample, such as, for example, a syringe barrel. Preferred holding means are conventional tubes or vials having a closed end and an open end. Such tubes may have an internal volume of 100 ul to 10 ml. Smaller tubes are generally used with a lancet for collection of very small quantities of blood by gravity flow. Representative of such tubes are Microtainer™ brand tubes supplied by Becton, Dickinson and Company.

The tube of the kit may also be an evacuated tube in which the open end is covered by a puncturable septum or stopper, such as Vacutainer™ brand tubes supplied by Becton Dickinson and Co. Evacuated tubes are generally used with a conventional tube holder and blood collection set for collection of multiple larger blood samples, and may contain any of a variety of conventional blood analysis additives, such as anticoagulants, blood clotting agents and serum separating gels. Preferred anticoagulants are citrate and ethylenediaminetetra acetic acid (EDTA). A preferred blood coagulant is a siliceous particle.

The holding means may also be a test strip in which the sample is allowed to flow directly onto a glass or plastic strip containing reagents for analysis, such as by immunoassay. A preferred test strip is a conventional blood meter strip containing hexokinase for glucose determination.

When a patient's skin is punctured in order to take a blood sample, the puncture wound is usually covered to stanch bleeding and protect the wound during healing. Accordingly, the kit of the invention may include an additional gauze to cover the wound and a means, such as adhesive, to affix the covering gauze over the wound.

In accordance with current medical practice, the kit preferably includes a disposable glove to avoid any contact between the phlebotomist and the sample. To promote blood flow, the kit may also include a tourniquet.

All components of the kit may be supplied in a packaging means, such as a compartmentalized plastic enclosure, preferably with a hermetically sealable cover so that the contents of the kit can be sterilized and sealed for storage.

Without being limited thereby, the FIGURE illustrates a typical package design for a kit of the invention contemplated for analysis of multiple samples as used, for example, in an adult blood test kit. Package 10 has outside frame 12 and integrally molded compartment separators 14 continuous therewith. Compartment 16 contains one or more gauze pads 18, at least one of which contains alcohol Compartment 20 contains a conventional blood collection set which includes a skin penetrating needle 22 and a delivery needle 23 both surrounded by a safety sleeve 24. Penetrating needle 22, preferably 21 gauge, is affixed to a housing 25 having wings 26 for gripping during needle insertion. A tubing 27 connects housing 25 with delivery needle 23, preferably 23 gauge, via a hub 28. Compartment 29 contains a conventional tube holder 30 therein Holder 30 has threads 31 for receiving needle hub 28. Compartment 32 contains one or more evacuated tubes 34 having septums 36 over open ends 38. Compartment 40 contains adhesive 42. Compartment 44 contains tourniquet 46. Compartment 50 contains a glove 52. While not shown in the drawing, the invention contemplates a hermetically sealed cover over the package. It will be apparent to one skilled in the packaging and molding arts that other designs having differently shaped compartments for different kit components can readily be envisioned. Thus, for example, evacuated tube 34 of the drawing may instead be a gravity actuated microtube and compartment 20 may contain a lancet instead of the blood collection set illustrated.

The package of the kit may be of any suitable plastic. Without wishing to be limited thereby, preferred plastics, suitable for molding, are thermoplastics such as polyethylene, polypropylene, polyvinyl chloride and copolymers thereof.

EXPERIMENTAL

The test kits below were constructed for the indicated purpose and contain the following components in a plastic package.

I Neonatal Kit
  a) alcohol gauze swab
  b) plain gauze
  c) lancet
  d) gravity actuated micro blood collection tube
  e) disposable gloves II Pediatric Kit
  a) alcohol gauze swab
  b) plain gauze
  c) 21 gauge double-ended needle with hub
  d) tube holder
  e) evacuated blood collection tube with anticoagulant
  f) evacuated blood collection tube with clotting activator and serum separating gel
  g) tourniquet
  h) disposable gloves III Adult Kit
  a) alcohol gauze swab
  b) plain gauze
  c) evacuated blood collection tube with anticoagulant
  d) evacuated blood collection tube with clotting activator and serum separating gel
  e) blood collection set
  f) tube holder
  g) disposable gloves
  h) tourniquet
  i) adhesive strip IV Diabetic Home Use Kit
  a) alcohol gauze swab
  b) plain gauze
  c) lancet
  d) adhesive strip
  e) blood glucose meter strip
  f) disposable gloves

What is claimed is:

1. A kit of materials for drawing a blood sample from a patient comprising:
  a) skin sterilizing means;
  b) gauze;
  c) holding means for a blood sample;
  d) skin penetrating means;
  e) means for delivery of said blood sample from said penetrating means to said holding means; and
  f) packaging means including a hermetically sealable cover whereby said kit is sterilizable.

2. The kit of claim 1 wherein said holding means is selected from the group consisting of a tube, vial, test strip and syringe barrel.

3. The kit of claim 1 wherein said skin penetrating means is a penetrating needle or a lancet.

4. The kit of claim 1 further comprising at least one item selected from the group consisting of a syringe plunger, a tourniquet, a glove, an adhesive strip and a tube holder.

5. The kit of claim 2 wherein said tube contains a reagent useful for blood analysis.

6. A kit of materials for drawing a blood sample from a neonatal patient comprising an alcohol swab, a plain swab, a lancet, a blood collection microtube and a glove.

7. A kit of materials for diabetic home care use comprising a lancet, an alcohol swab, an adhesive strip, a blood meter strip, a plain gauze and glove and packaging means including a hermetically sealable cover whereby said dit is sterilizable.

8. A kit of materials for drawing a blood sample from a pediatric patient comprising an alcohol swab, a plain gauze, a 21 gauge double-ended needle with hub, a tube holder, a tourniquet, a glove, an evacuated blood collection tube containing an anticoagulant, and an evacuated blood collection tube containing a clotting activator and a serum separating gel.

9. A kit of materials for drawing a blood sample from an adult patient comprising an alcohol swab, a plain gauze, a blood collection set, a tube holder, a tourniquet, a glove, an adhesive, an evacuated blood collection tube containing an anticoagulant and an evacuated tube containing a clotting activator and a serum separating gel.

10. A kit of materials for drawing a blood sample from a patient comprising:
  a) skin sterilizing means;
  b) gauze;
  c) holding means for a blood sample:
  d) skin penetrating means;
  e) a blood collection set;
  f) at least one item selected from the group consisting of a syringe plunger, a tourniquet, a glove, an adhesive strip and a tube holder; and
  g) packaging means including a hermetically sealable cover whereby said kit is sterilizable.

* * * * *